US 6,693,197 B2

United States Patent
Chan et al.

(10) Patent No.: US 6,693,197 B2
(45) Date of Patent: Feb. 17, 2004

(54) PROCESS FOR THE SYNTHESIS OF DERIVATIVES OF 2,3-DIHYDRO-1,4-DIOXINO- [2,3-F] QUINOLINE

(75) Inventors: Anita W. Chan, Fort Lee, NJ (US); Timothy T. Curran, Whitmore Lake, MI (US); Silvio Iera, Montreal (CA); Warren Chew, Outremont (CA); John H. Sellstedt, Lachine (CA); Galina Vid, New City, NY (US); Gregg Feigelson, Monsey, NY (US); Zhixian Ding, Fort Lee, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/145,369

(22) Filed: May 14, 2002

(65) Prior Publication Data

US 2002/0187983 A1 Dec. 12, 2002

Related U.S. Application Data

(60) Provisional application No. 60/291,547, filed on May 17, 2001.

(51) Int. Cl.[7] .................... C07D 491/02; C07D 519/00
(52) U.S. Cl. ............................................ 546/90; 546/80
(58) Field of Search ...................... 546/90, 80

(56) References Cited

U.S. PATENT DOCUMENTS

| | | | |
|---|---|---|---|
| 5,318,988 A | 6/1994 | Schohe-Loop et al. | |
| 5,371,094 A | 12/1994 | Heine | |
| 5,741,789 A | 4/1998 | Hibschman et al. | |
| 5,756,532 A | 5/1998 | Stack et al. | |
| 5,869,490 A | 2/1999 | Stack | |
| 5,962,465 A | 10/1999 | Stack et al. | |
| 6,458,802 B1 * | 10/2002 | Tran et al. .................. | 514/291 |

FOREIGN PATENT DOCUMENTS

WO    WO 02/072587 A1    9/2002

OTHER PUBLICATIONS

Victor Perez et al., The Lancet, May 1997, 1594–1597, 349.
Karen E. Torraca et al., J. Am.Chem. Soc., 2000, 12907–12908, 122.
Marcel Hibert et al., J. Chem. Soc. Chem. Commun., 1986, 1432–1433.
Alain Godard et al., J. Organomet. Chem., 1987, 1–12, 336.
Joh. Howitz et al., Chem. Ber., 1905, 1260–70.
Joh. Howitz et al., Chem. Ber., 1903, 456–466.
Robert C. Elderfield et al., J. Am. Chem. Soc., 1946, 1584–7, 68.
Joh. Howitz et al., Chem. Ber., 1905, 887–892, 38.
Jean Albert Gautier et al., Bull. Soc. Chim. Fr., 1967, 3190–5.

* cited by examiner

Primary Examiner—Charanjit S. Aulakh
(74) Attorney, Agent, or Firm—Woodcock Washburn LLP

(57) ABSTRACT

Methods of preparing compounds of Formula I

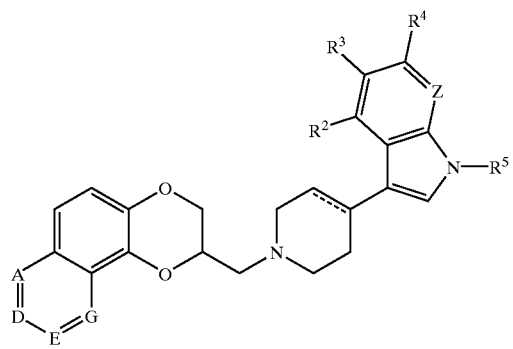

are provided.

38 Claims, No Drawings

PROCESS FOR THE SYNTHESIS OF DERIVATIVES OF 2,3-DIHYDRO-1,4-DIOXINO- [2,3-F] QUINOLINE

This application claims priority from co-pending provisional application Ser. No. 60/291,547, filed on May 17, 2001, the entire disclosure of which is hereby incorporated by reference.

FIELD OF THE INVENTION

This invention relates to a novel process of producing derivatives of 2,3-dihydro-1,4-dioxino [2,3-f]quinoline in a highly convergent and efficient manner, as well as intermediates thereof. Compounds of the present invention are SSRI/5-HT$_{1A}$ antagonists useful for the treatment of diseases which are caused or affected by disorders of the serotonin-affected neurological systems such as depression, including childhood depression, obsessive compulsive disorders, panic disorder, generalized anxiety disorder, social anxiety disorders, sexual dysfunction, eating disorders such as bulimia, obesity, addictive disorders caused by ethanol or cocaine abuse and dysthymia as described in copending application Ser. No. 60/275,564 filed Mar. 14, 2001.

SUMMARY OF THE INVENTION

In accordance with the present invention is provided methods of making compounds of Formula I:

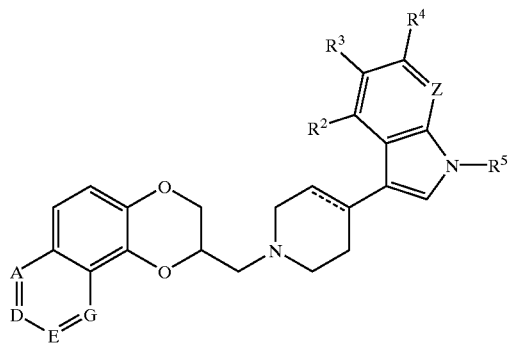

I wherein
  $R^1$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
  $R^2, R^3, R^4$, and $R^6$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms
  $R^5$ is hydrogen or alkyl of 1 to 6 carbon atoms;
  A dotted line represents an optional double bond;
  A and D are selected from carbon, substituted by $R^1$, and nitrogen, provided that at least one of A and D is nitrogen;
  E and G are carbon, substituted by $R^1$; and
  Z is N or $CR^6$;

or pharmaceutically acceptable salts thereof, comprising the steps of:

a) halogenating a compound of the formula:

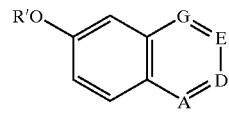

2 wherein R' is alkyl of 1–6 carbon atoms;

with a halogenating reagent to afford a compound of the formula:

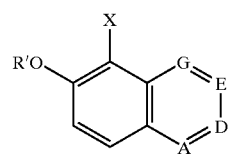

3 wherein X is Br, Cl, or I;

b) dealkylating the compound of Formula 3 in an acid to afford a compound of the formula:

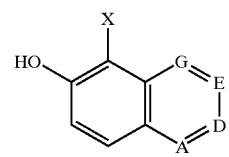

4 c) alkylating the compound of Formula 4 with R" protected glycidyl ethers

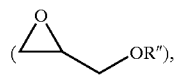

wherein R" is benzyl or substituted benzyl to afford compound of the formula:

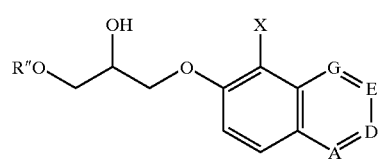

5 d) cyclizing the compound of Formula 5 with palladium or copper catalyst to afford a compound of the formula:

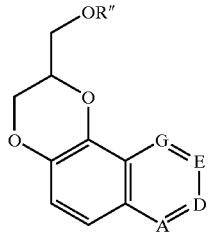

6 e) debenzylating the compound of Formula 6 to afford the compound of the formula:

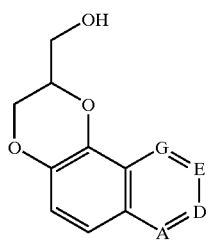

7 f) activating the hydroxy moiety of the compound of Formula 7 with a sulfonating reagent to afford a compound of the formula:

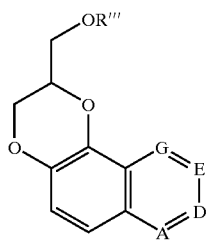

8 wherein R''' is an aryl-, or alkyl-sulfonate and g) coupling the compound of Formula 8 with the appropriate azaheterocycle of Formula 9

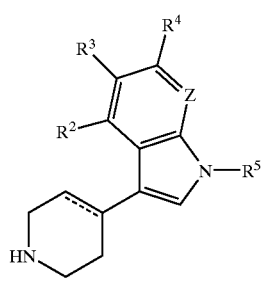

9 in the presence of base to provide a compound of Formula I.

In alternative embodiments of the present invention the hydroxy moiety of compounds of Formula 7 may be activated to halide to afford a compound of the formula:

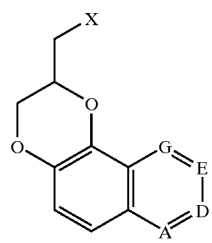

10 wherein X is I, Br, or Cl and the compound of Formula 10 may be coupled with the appropriate azaheterocycle of Formula 9

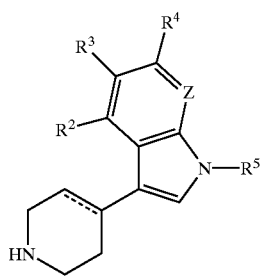

9 in the presence of base to provide a compound of Formula I.

In other embodiments of the present invention are provided methods of making compounds of Formula I

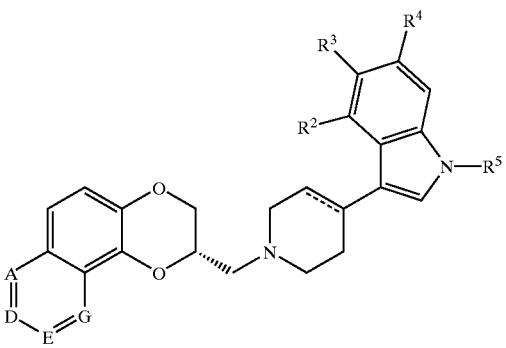

I comprising the steps of:

a) halogenating a compound of the formula:

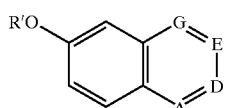

2 wherein R' is alkyl of 1–6 carbon atoms;

with a halogenating reagent in a solvent to afford a compound of the formula:

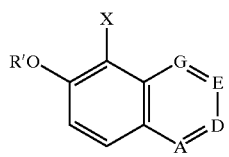

3 wherein X is Br, Cl, or I;

b) dealkylating the compound of Formula 3 in an acid to afford a compound of the formula:

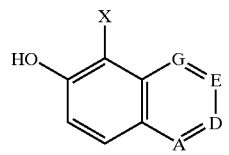

4 c) alkylating the compound of Formula 4 with R" protected glycidyl ethers

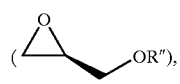

wherein R" is benzyl or substituted benzyl to afford compound of the formula:

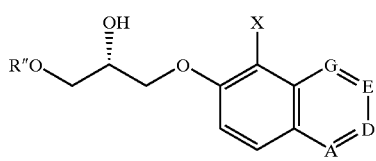

5 d) cyclizing the compound of Formula 5 with palladium or copper catalyst to afford a compound of the formula:

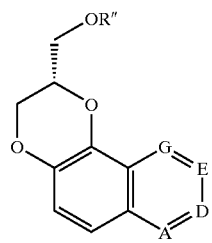

6 e) debenzylating the compound of Formula 6 to afford the compound of the formula:

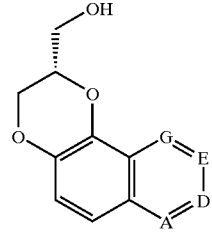

7 f) activating the hydroxy moiety of the compound of Formula 7 with a sulfonating reagent to afford a compound of the formula:

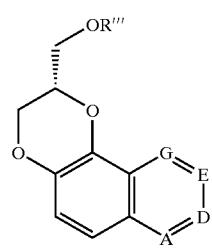

8 wherein R''' is an aryl- or alkyl-sulfonate; and g) coupling the compound of Formula 8 with the appropriate azaheterocycle of Formula 9

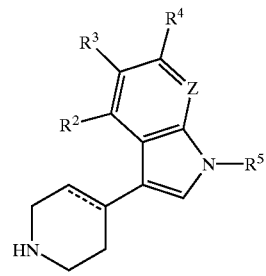

9 in the presence of base to provide a compound of Formula I.

In alternative embodiments of the present invention the hydroxy moiety of compounds of Formula 7 may be activated to halide to afford a compound of the formula:

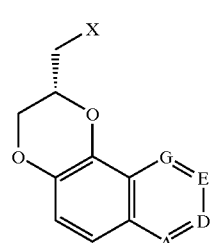

10 wherein X is I, Br, or Cl and the compound of Formula 10 may be coupled with the appropriate azaheterocycle of Formula 9

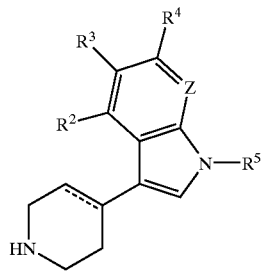

9 in the presence of base to provide a compound of Formula I.

In some embodiments of the present invention is provided a method of making a compound of Formula Ia

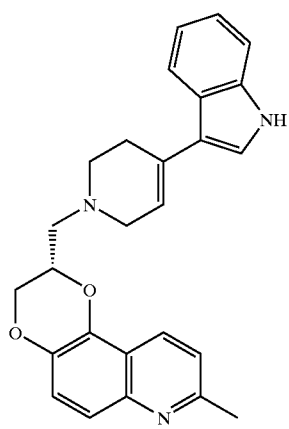

Ia comprising the steps:

a) halogenating a compound of the formula:

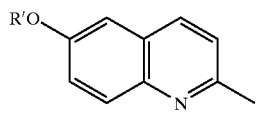

2a wherein R' is alkyl of 1–6 carbon atoms;

with a halogenating reagent to afford a compound of the formula:

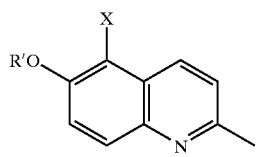

3a wherein X is Br, Cl, or I;

b) dealkylating the compound of Formula 3a in an acid to afford a compound of the formula:

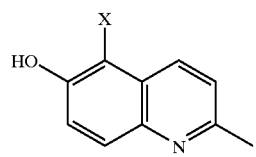

4a c) alkylating the compound of Formula 4a with R″ protected glycidyl ethers

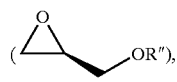

5 wherein R″ is benzyl or substituted benzyl; to afford a compound of the formula:

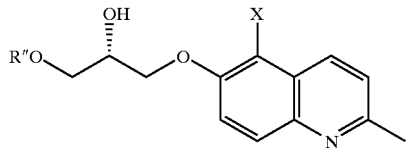

5a d) cyclizing the compound of Formula 5a with palladium or copper catalyst to afford a compound of the formula:

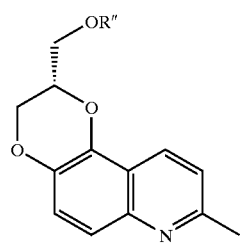

6a e) debenzylating the compound of Formula 6a to afford a compound of the formula:

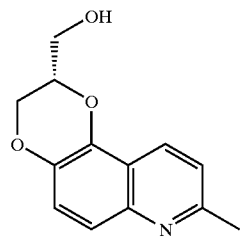

7a f) activating the hydroxy moiety of the compound of Formula 7a with a sulfonating reagent to afford a compound of the formula:

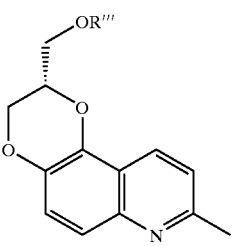

8a wherein R‴ is an aryl- or alkyl-sulfonate; and g) coupling the compound of Formula 8a with 3-tetrahydropyridinyl-indole in the presence of base to provide a compound of Formula Ia.

Alternatively, the hydroxy moiety of compounds of Formula 7a may be activated to halide to afford a compound of Formula 10a

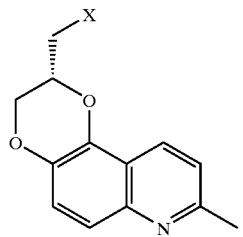

10a wherein X is I, Br, or Cl and the compound of Formula 10a may be coupled with 3-tetrahydropyridinyl-indole in the presence of base to provide a compound of Formula Ia.

In accordance with other aspects of the invention is provided a method of preparing compounds of Formula 5:

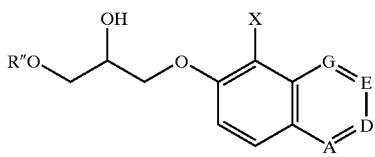

5 wherein A, D, E, G, X and R" are as defined for Formula I and R" is benzyl or substituted benzyl, comprising alkylating the compound of Formula 4

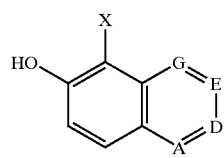

4 with R" protected glycidyl ethers

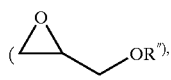

wherein R" is benzyl or substituted benzyl. In some embodiments of the invention A is nitrogen, D is carbon substituted with methyl, and E and G are unsubstituted carbon.

Further in accordance with the present invention is provided a method of preparing compound of Formula 6

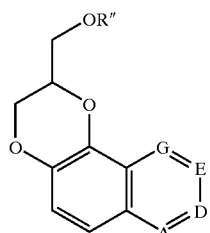

6 where A, D, E and G are as defined for Formula I, and R" is benzyl or substituted benzyl, comprising the step of cyclizing a compound of Formula 5

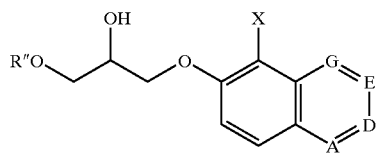

5 with palladium or copper catalyst. In some embodiments of the invention A is nitrogen, D is carbon substituted with methyl, and E and G are unsubstituted carbon.

Further in accordance with the invention is provided a method of preparing compound of Formula 8

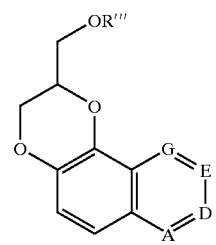

8 wherein A, D, E and G are defined as for Formula I and R''' is an aryl- or alkyl-sulfonate; comprising activating the hydroxy moiety of the compound of Formula 7

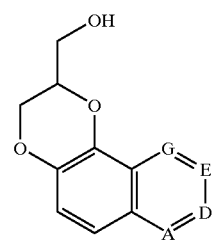

7 with a sulfonating reagent. In some embodiments of the invention A is nitrogen, D is carbon substituted with methyl, and E and G are unsubstituted carbon.

Further in accordance with the invention is provided a method of preparing compound of Formula 10

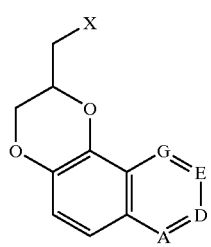

10 wherein A, D, E and G are as defined for Formula I, and X is I, Cl or Br, comprising activating compound of Formula 7

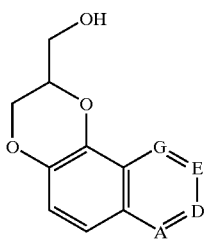

to halide with halophosphorous such as phosphorous triiodide, phosphorous tribromide or phosphorous pentachloride, or with thionyl halide or any standard halogenating reagent.

Further in accordance with the present invention is provided a method of preparing compound of Formula 7

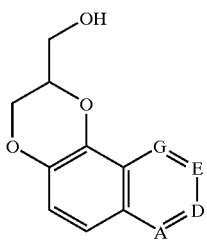

wherein A, D, E and G are as defined Formula I, comprising debenzylating a compound of Formula 6

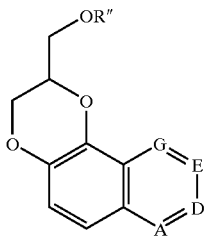

where R" is benzyl or substituted benzyl.

In some embodiments of the invention A is nitrogen, D is carbon substituted with methyl and E and G are unsubstituted carbon.

In some embodiments of the invention compound of Formula 2

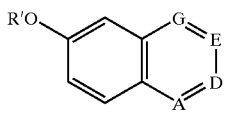

is halogenated with a halogenating agent such as N-halosuccinimide wherein halo means bromo-, chloro-, or iodo- in a suitable solvent such as acetonitrile.

In other embodiments of the invention compound of Formula 3

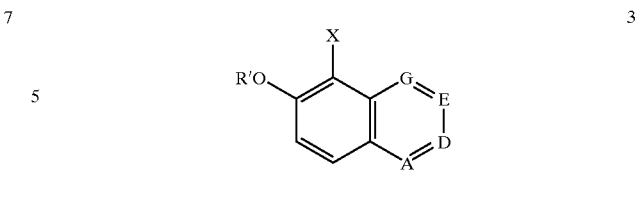

is demethylated with a Lewis acid in a solvent or a strong protic acid. Preferred Lewis acids include, but are not limited to, boron tribromide, boron trichloride, aluminum trichloride, ferric chloride, trimethylsilyl iodine. The preferred solvent is methylene chloride. Strong protic acids include, but are not limited to, HBr and HCl.

Compound of Formula 4

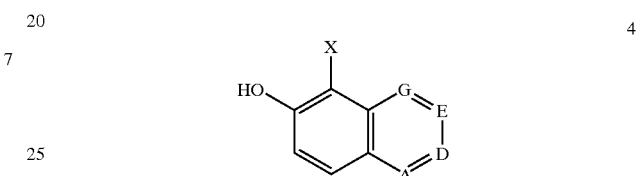

may be alkylated with R" protected glycidyl ethers

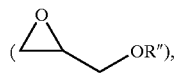

wherein R" is benzyl or substituted benzyl in a polar solvent. For instance R" may be benzyl, 4-bromobenzyl, 4-chlorobenzyl, 3,4-dimethoxybenzyl, 2- or 4-nitrobenzyl, or 4-methoxyphenyl.

Exemplary polar solvents useful in alkylation of compounds of Formula 4 include dimethylsulfoxide (DMSO), dimethylforamide (DMF), dimethylacetamide (DMA).

Alkylation may be performed in the presence of a base such as, but not limited to, triethylamine, sodium carbonate, or potassium carbonate.

Compound of Formula 5 can be cyclized using palladium catalysts such as, but not limited to, tris(dibenzylideneacetone)dipalladium, tetrakis(triphenylphosphine)palladium, or palladium acetate with phosphine ligands including but not limited to (±) 2,2'-bis(diphenylphosphino)-1,1'-binaphthyl (BINAP) and separate enantiomers thereof; (±) 2,2'-bis(di-p-tolyl-phosphino)-1,1'-binaphthyl (Tol-BINAP) and separate enantiomers thereof; 1-1'-bis(diphenylphosphino)ferrocene; 1,3-bis(diphenylphosphino)propane; and 1,2 bis(diphenylphosphino)ethane in the presence of bases such as sodium hydride (NaH), lithium hydride (LiH), potassium hydride (KH), potassium carbonate, sodium carbonate, titanium carbonate, cesium carbonate, potassium t-butoxide or potassium phosphate tribasic in suitable solvent such as toluene.

Alternatively, compound of Formula 5 can be cyclized with copper catalyst such as copper iodide in the presence of bases such as NaH, LiH, KH in a suitable solvent such as toluene.

Debenzylation of compound of Formula 6 can be carried out with Lewis acids such as boron tribromide, boron trichloride, aluminum trichloride, ferric chloride, trimethylsilyl iodine in a suitable solvent such as methylene chloride.

Debenzylation of compound of Formula 6 may also be carried out with strong protic acids such as HBr and HCl, or alternatively, under reductive cleavage conditions using Pd catalyst and hydrogen transfer reagents such as hydrogen, cyclohexene, methyl cyclohexene, or ammonium formate.

The hydroxy moiety of compound of Formula 7 is activated with a sulfonating reagent such as aryl or alkyl sulfonyl chloride or alkyl or aryl sulfonic anhydride in the presence of a base such as triethylamine or pyridine in suitable solvents such as methylene chloride, tetrahydrofuran (THF), or toluene. Alkyl, as used herein preferably refers to alkyl of 1–6 carbon atom. Aryl, as used herein preferably refers to phenyl. Preferred sulfonating reagents include, but are not limited to p-toluenesulfonyl chloride, methanesulfonyl chloride, 2-, 3- or 4-nitrobenzenesulfonyl chloride, 2- or 4-bromo-benzenesulfonyl chloride, or trifluoromethylsulfonic anhydride.

Alternatively the hydroxy moiety of compound of Formula 7 is activated as halogen, such as 1, Br or Cl with reagent such as $I_3P$, $Br_3P$ $Cl_5P$ or $SOCl_2$ to provide compound of Formula 10.

Compound of Formula 8 or 10 are coupled with azaheterocycles of Formula 9 including 3-tetrahydropyridinyl-indole in the presence of bases such as sodium carbonate, potassium carbonate, or Hünig's base in suitable polar solvents such as THF, dioxane, DMSO, DMF, or DMA to afford compound of Formula I.

Still further in accordance with the present invention are provided novel intermediates of the formula

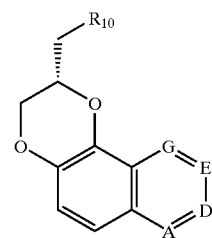

wherein:

$R_7$ is hydroxy, alkoxy of 1–6 carbon atoms, or alkoxy of the formula

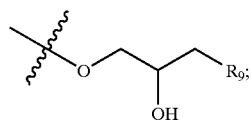

wherein $R_9$ is hydroxy, benzyl ether, substituted benzyl ethers such as 4-bromo-benzyl ether, 4-chlorobenzyl ether, 3,4-dimethoxybenzyl ether, 2- or 4-nitrobenzyl ether, or 4-methoxyphenyl; and $R_8$ is halogen or hydrogen; and salts thereof.

A is nitrogen and D is carbon in preferred intermediates of Formula II.

Also in accordance with the present invention are novel intermediates of the formula

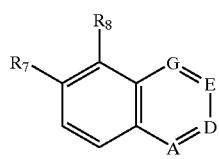

wherein:

$R_{10}$ is hydroxy, halide or aryl or alkyl sulfonates; and salts thereof.

A is nitrogen and D is carbon in preferred intermediates of Formula III.

Certain compounds of the present invention contain one asymmetric carbon atom, giving rise to enantiomeric forms of the compounds. It is to be understood that the invention encompasses the enantiomers thereof including racemic mixtures.

It is known that compounds possessing a basic nitrogen can be complexed with many different acids (both protic and non-protic). The invention also includes acceptable salt forms formed from the addition reaction with either inorganic or organic acids. Inorganic acids such as hydrochloric acid (HCl), hydrobromic acid (HBr), hydroiodic acid (HI), sulfuric acid, phosphoric acid, nitric acid are useful as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful.

"Halo" as used herein, such as in the term "halosuccinimide" refers to halogen and preferably bromo-, chloro-, or iodo-.

DETAILED DESCRIPTION OF INVENTION

Thus, in accordance with the present invention is provided a process for preparing in high yield enantiomerically pure compounds of Formula I as well as intermediate thereof.

The process of the present invention can be illustrated by the following reaction scheme (Scheme I), wherein A, D, E, G, R', R", R'", and X are as stated above. The reagents and the solvents for the individual step are given for illustrative purposes only and may be replaced by reagents and solvents known to those skilled in the art.

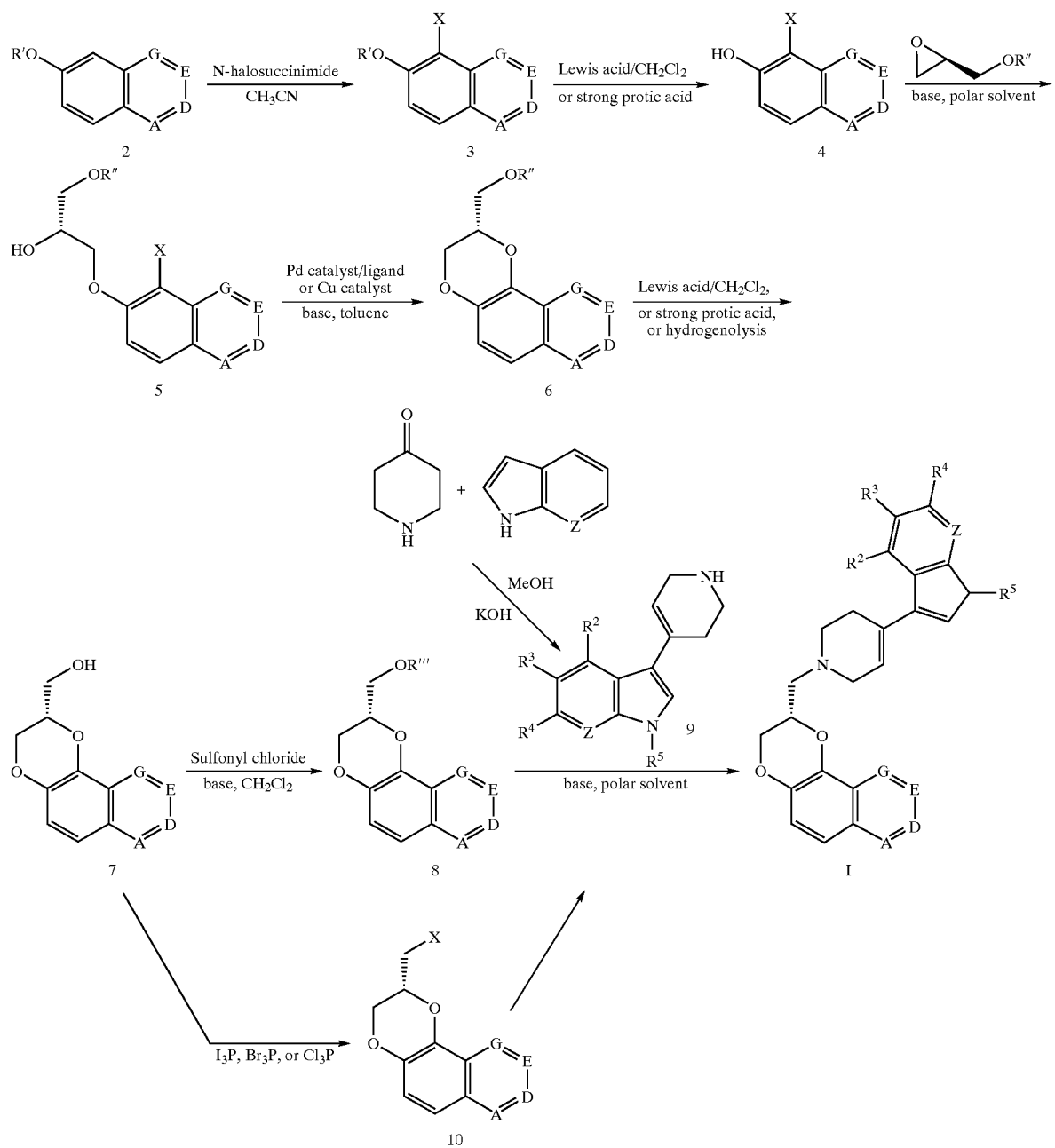

Scheme I

This process is characterized by high yields and purity of the products and technical convenience. The synthesis of compound I comprises steps that begin with halogenation of 2 with halogenating reagents such as N-halosuccinimide in acetonitrile to give 3. Deprotecting 3 with Lewis acids such as boron tribromide, boron trichloride, aluminum trichloride, ferric chloride, or trimethylsilyl iodide in a suitable solvent such as methylene chloride, or with strong protic acids such as HBr and HCl to give the salt of 4. Free base 4 is very water soluble and neutralization is achieved from an Amberlyst A-21 resin slurry in polar solvents such as ethanol or methanol.

Alkylation of 4, either as the free base or as the salt, with benzyl or substituted benzyl protected glycidyl ethers in suitable polar solvents such as dimethylsulfoxide (DMSO), dimethylformamide (DMF), or dimethyl acetamide (DMA) in the presence of bases such as sodium carbonate, potassium carbonate, or triethylamine gives 5.

Compound 5 is cyclized using palladium catalysts such as tris-(dibenzylideneacetone)dipalladium, tetrakis (triphenylphosphine)palladium, or palladium acetate with ligands from the group consisting of (±) 2,2'-bis (diphenylphosphino)-1,1'-binaphthyl (BINAP) and separate enantiomers thereof; (±) 2,2'-bis(di-p-tolylphosphino)-1,1'-binaphthyl (Tol-BINAP) and separate enantiomers thereof; 1-1'-bis(diphenyl-phosphino) ferrocene; 1,3-bis(diphenyl-phosphino)propane; and 1,2-bis(diphenyl-phosphino)ethane in the presence of bases such as NaH, LiH, KH, potassium carbonate, sodium carbonate, titanium carbonate, cesium carbonate, potassium t-butoxide or potassium phosphate tribasic in suitable solvent such as toluene; or alternatively, with copper catalyst such as copper iodide in the presence of bases such NaH, LiH, KH in a suitable solvent such as toluene to afford quinoline 6. Similar dioxanes may also be prepared using the above reagents.

Deprotection of quinoline 6 with Lewis acids such as boron tribromide, boron trichloride, aluminum trichloride, ferric chloride, trimethylsilyl iodide in a suitable solvent such as methylene chloride, or with strong protic acids such as HBr and HCl or under reductive cleavage conditions using Pd catalyst and hydrogen transfer reagents such as hydrogen, cyclohexene, methyl cyclohexene, or ammonium formate to gives 7. The hydroxyl moiety of 7 can be activated with a sulfonating reagent such as an aryl or alkyl sulfonyl chloride or aryl or alkyl sulfonic anhydride such as p-toluenesulfonyl chloride, methanesulfonyl chloride, 2-, 3- or 4-nitro-benzenesulfonyl chloride, 2- or 4-bromobenzenesulfonyl chloride, or trifluoromethylsulfonic anhydride in the presence of bases such as triethylamine or pyridine in suitable solvents such as methylene chloride, THF, or toluene to afford 8. The final coupling of 8 with azaheterocycle 9, prepared by reaction of indole with the hydrochloride salt of 4-piperidone, in the presence of bases such as Hunig's base, potassium carbonate, or sodium carbonate in polar solvents such as THF, dioxane, DMSO, DMF, or DMA affords final compound I.

The following examples illustrate the process of the present invention but are not meant to be limiting thereof.

EXAMPLE 1

Preparation of 5-Bromo-6-Methoxy-2-Methylquinoline

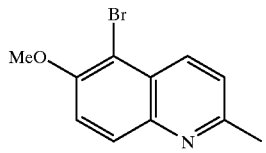

A solution of 6-methoxy-2-methylquinoline (177 g, 1.02 mol) in acetonitrile (1.77 L) was cooled to 0–3° C. followed by portion-wise addition of N-bromosuccinimide (200 g, 1.12 mol) over a period of 30 min while maintaining the same temperature. The resulted brown slurry was warmed to ambient temperature and stirred for an additional 6 h. The reaction was then quenched by a 10% $NaHSO_3$ solution (211 mL). The reaction mixture was concentrated to a volume of 600 mL then slowly poured into 0.1 N NaOH (2.5 L). The slurry (pH=9) was stirred at room temperature for 1 h then filtered, washed with water (2×1 L) and dried in a vacuum oven to give 253 g (98.6%) of the title compound as a brown solid.

$R_f$=0.39 (3:7) EtOAc:heptane;

$^1$H NMR (DMSO) δ8.30 (d, J=6.5 Hz, 1H), 7.98 (d, J=6.9 Hz, 1H), 7.70 (d, J=7.0 Hz, 1H), 7.47 (d, J=6.5 Hz, 1H), 4.02 (s, 3H), 2.66 (s, 3H);

$^{13}$C NMR (DMSO) δ156.9, 153.1, 143.2, 133.6, 129.3, 126.0, 123.6, 117.0, 106.1, 56.9, 24.3;

IR (KBr): $\upsilon_{max}$ 3435, 3197, 2943, 2843, 1699, 1613, 1599, 1495, 1342, 1305, 1267, 1131, 1067, 968, 870, 811, 629 $cm^{-1}$;

Analysis for $C_{11}H_{10}NOBr$: Calculated: C, 52.40; H, 3.97; N, 5.56. Found: C, 52.13; H, 3.94; N, 5.61.

EXAMPLE 2

Preparation of the Hydrobromide Salt of 5-Bromo-2-Methyl-6-Quinolinol

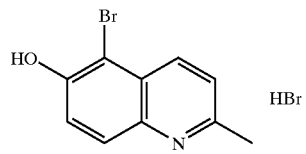

A mixture of 5-bromo-2-methyl-6-methoxyquinoline (30 g, 0.12 mol) in 48% HBr (135 mL) was heated to reflux for 7 h then cooled to 5° C. in 1 h to give a brown and thick slurry. The slurry was stirred at 0–5° C. for 1 h then filtered, washed with EtOAc (2×50 mL) and dried in a vacuum oven to give 34.9 g (92%) of the title compound as a brown solid.

$^1$H NMR (DMSO) δ8.26 (d, J=8.7 Hz, 1H), 7.85 (d, J=9.1 Hz, 1H), 7.56 (d, J=9.1 Hz, 1H), 7.45 (d, J=8.7 Hz, 1H), 2.64 (s, 3H);

$^{13}$C NMR (DMSO) δ155.7, 152.0, 142.8, 133.3, 128.9, 126.4, 123.3, 121.2, 103.3, 24.1.

EXAMPLE 3

Preparation of 5-Bromo-2-Methyl-6-Quinolinol

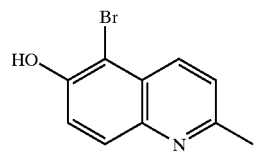

A slurry of the hydrobromide salt of 5-bromo-2-methyl-6-quinolinol (3.4 g, 10.5 mmol) and Amberlyst A-21 ion-exchange resin (1.7 g, pre-washed with MeOH then dried in oven) in MeOH (35 mL) was stirred at room temperature for 3 h. The mixture was then filtered and concentrated in vacuo to give 2.5 g (100%) of a yellow solid.

$R_f$=0.36 (1:1) EtOAc:heptane;

$^1$H NMR (DMSO) δ8.26 (d, J=8.4 Hz, 1H), 7.82 (d, J=9.3 Hz, 1H), 7.47 (t, J=9.1 Hz, 2H), 2.66 (s, 3H);

EXAMPLE 4

Preparation of (2S)-1-(Benzyloxy)-3-[(5-Bromo-2-Methyl-6-Quinolinyl)Oxyl]-2-Propanol

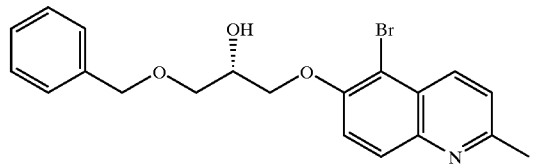

A solution of 5-bromo-2-methyl-6-quinolinol (30.1 g, 126 mmol), (R)-benzyl glycidyl ether (24.9 g, 152 mmol) and triethylamine (17.4 g, 172 mmol) in DMA (200 mL) was heated in a 95–98° C. oil bath for 2 days. The solution was cooled and poured into water (300 mL) while stirring. The tan precipitate formed was filtered, washed with water (100 mL) and dried in a vacuum oven to give 37 g (73%) of the title compound as a tan solid.

$R_f$=0.35 (EtOAc);

$^1$H NMR (DMSO) δ8.31 (d, J=8.8 Hz, 1H), 7.96 (d, J=9.2 Hz, 1H), 7.72 (d, J=9.3 Hz, 1H), 7.74 (d, J=8.7 Hz, 1H), 7.25–7.36 (m, 5H), 5.28 (d, J=5.1 Hz, 1H), 4.56 (s, 2H), 4.22–4.29 (m, 2H), 4.08–4.15 (m, 1H), 3.61–3.73 (m, 2H), 2.66 (s, 3H);

$^{13}$C NMR (DMSO) δ157.0, 152.7, 143.4, 138.4, 133.7, 129.2, 128.1, 127.4, 127.3, 126.0, 123.6, 118.4, 106.8, 72.4, 71.3, 71.2, 68.1, 24.3;

IR (KBr): $υ_{max}$ 3391, 3188, 2938, 2875, 1597, 1497, 1268, 1061, 817, 697 cm$^{-1}$;

Specific rotation=+6.2° (c=1, CH$_3$OH);

Analysis for C$_{20}$H$_{20}$BrNO$_3$: Calculated: C, 59.66; H, 4.97; N, 3.48. Found: C, 59.43; H, 4.97; N, 3.55.

EXAMPLE 5

Preparation of (2S)-1-(Benzyloxy)-3-[5-Bromo-2-Methyl-6-Quinolinyl)Oxyl]-2-Propanol from 5-Bromo-2-Methyl-6-Quinolinol Salt

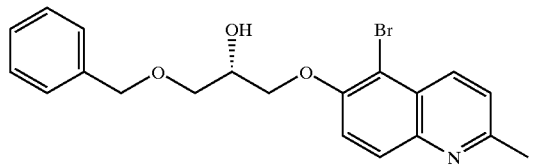

In a rapidly stirred mixture of K$_2$CO$_3$ (597 g, 4.32 mol)) in DMF (3 L), HBr salt of 5-bromo-2-methyl-6-quinolinol (551 g, 1.73 mol) was added over 30–60 min at rt. After cooling the mixture to room temperature, (R)-benzyl glycidyl ether (353 g, 2.07 mol) was added rapidly. The reaction mixture was then heated to 70° C. for from 50–70 h before cooling to 20–23° C. Water (6.05 L) was added over a period of 30–120 min. The reaction mixture was filtered and the filtered cake was washed with additional water (1 L). The solid was then stirred in water (3 L) for 30–40 min and filtered. The filtered cake was washed with water (1 L). The solid obtained was then dried in a vacuum oven (5–0.5 mm Hg) at 65° C. over 8–16 h to give 662 g of the title compound. The crude product was then recrystallized in EtOH (2.5 L) to give 487 g (70%) of the title compound as an off-white solid.

EXAMPLE 6

Palladium Catalyzed Preparation of (2S)-2[(Benzyloxy)methyl]-8-methyl-2,3-Dihydro[1,4]Dioxino[2,3-f]Quinoline

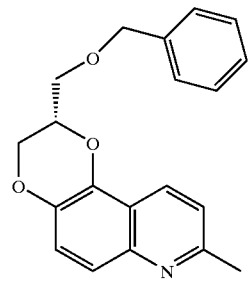

A solution of (2S)-1-(benzyloxy)-3-[5-bromo-2-methyl-6-quinolinyl)oxyl]-2-propanol (10 g, 24.9 mmol), potassium phosphate tribasic (11.4 g, 50 mmol), Pd(OAc)$_2$ (280 mg, 1.25 mmol) and racemic BINAP (1.55 g, 2.49 mmol) in toluene (50 mL) was heated in a 100–102° C. oil bath for 3 d. The solution was cooled to room temperature then EtOAc (50 mL) and water (50 mL) were added. The reaction mixture was filtered through a bed of celite. The two layers were separated. The aqueous layer was extracted with EtOAc (30 mL). The combined organic layers were dried over Na$_2$SO$_4$, filtered and concentrated in vacuo to give 8 g (100%) of the crude product as a brown syrup. The crude product can be carried through the debenzylation step before purification. A sample of the crude mixture was purified on SiO$_2$, eluted with (3:1) hexane:EtOAc gave the title compound as a yellow oil which solidified upon standing.

$R_f$=0.5 (EtOAc);

$^1$H NMR (DMSO) δ8.24 (d, J=8.6 Hz, 1H), 7.46 (d, J=9.2 Hz, 1H), 7.27–7.38 (m, 7H);

$^{13}$C NMR (DMSO) δ156.4, 143.3, 138.1, 137.9, 135.2, 128.4, 128.2, 127.2, 127.4, 121.4, 121.0, 120.9, 118.1, 72.5, 72.4, 68.2, 65.1, 24.5;

IR (KBr): $υ_{max}$ 3413, 3280, 3028, 2917, 2886, 3798, 1628, 1601, 1572, 1485, 1453, 1374, 1257, 1100, 1056, 982 cm$^{-1}$;

Specific Rotation=+7.9° (c=1.2, CHCl$_3$);

Analysis for C$_{20}$H$_{19}$NO$_3$: Calculated: C, 74.68; H, 5.91; N, 4.36. Found: C, 74.48; H, 6.03; N, 4.14.

EXAMPLE 7

Copper Catalyzed Preparation of (2S)-2[(Benzyloxy)methyl-8-methyl-2,3-Dihydro[1,4]Dioxino[2,3-f]Quinoline

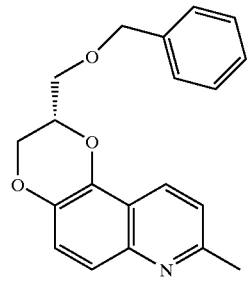

To a mixture of (2S)-1-(benzyloxy)-3-[5-bromo-2-methyl-6-quinolinyl)oxyl]-2-propanol (100 g, 0.249 mol) and copper (I) iodide (47.4 g, 0.249 mol) in toluene (2 L), NaH (10.9 g, 0.45 mol) was added in portions at 30–35° C. over 20 min. The reaction mixture was kept at 35° C. for 30 min then heated to 110° C. slowly. After 30 min, the reaction was cooled to 60OC, additional NaH (10.9 g, 0.45 mol) was added. This was warmed to 110° C. for an additional 2 hours then cooled to rt before dropwise addition of water (200 mL). After stirring for ~15 min, the mixture was filtered through a bed of celite then washed with toluene (3×50 mL) and water (50 mL). The two layers were separated. The organic layer was extracted with water (100 mL), NH$_4$OH (100 mL), 25% NaCl (100 mL) and concentrated in vacuo to give 387.6 g of the crude product as a brown syrup. The crude product was carried through to the debenzylation step before purification (see example 10).

EXAMPLE 8

Lewis Acid Catalyzed Preparation of [(2R)-8-Methyl-2,3-Dihydro[1,4]Dioxino[2,3-f]Quinolin-2-yl]Methanol

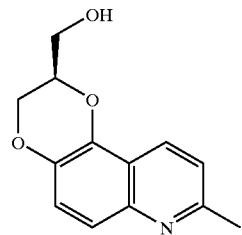

To a solution of (2R)-2[(benzyloxy)methyl-8-methyl-2,3-dihydro[1,4]dioxino [2,3-f]quinoline (0.74 g, 2.3 mmol) in $CH_2Cl_2$ (16 mL) being cooled in an ice-bath, $FeCl_3$ (1.9 g, 12 mmol) was added. After 1 h, the ice-bath was removed and the reaction mixture was stirred for another 17 h. $CHCl_3$ (30 mL) and 1 N NaOH (50 mL) were added to result in a suspension which was then filtered. The filtered solid was washed with $CH_3OH$ (50 mL). The combined organic layers were concentrated in vacuo. Purification on $SiO_2$, eluted with (10:1) $CHCl_3$:iPrOH gave 0.45 g (84%) of the title compound as an off-white solid.

$R_f$=0.34 (EtOAc);

$^1$H NMR (DMSO) δ8.29 (d, J=6.6 Hz, 1H), 7.42 (d, J=6.6 Hz, 1H), 7.30–7.37 (m, 2H), 5.13 (t, J=4.3 Hz, 1H), 4.43–4.46 (m, 1H), 4.31–4.33 (m, 1H), 4.09–4.14 (m, 1H), 3.70–3.78 (m, 2H), 2.60 (s, 3H);

$^{13}$C NMR (DMSO) δ156.7, 143.6, 138.4, 135.9, 129.0, 121.7, 121.4, 121.1, 118.5, 78.4, 74.4, 65.6, 60.3, 24.9;

IR (KBr): $v_{max}$ 3200, 2917, 2849, 1628, 1601, 1488, 1374, 1341, 1265, 1107, 1079, 1050, 809 cm$^{-1}$;

GC/MS 231, 212, 200, 186, 175, 168, 156, 145, 129, 117, 110, 102, 89, 76, 64, 57, 50, 39, 31.

EXAMPLE 9

Palladium Catalyzed Preparation of [(2S)-8-Methyl-2,3-Dihydro[1,4]Dioxino[2,3-f]Quinolin-2-yl]Methanol

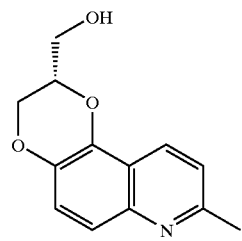

To a solution of (2S)-2[(benzyloxy)methyl-8-methyl-2,3-dihydro[1,4]dioxino [2,3-f]quinoline (0.16 g, 0.5 mmol) in EtOH (1 mL) was added cyclohexene (0.5 mL) then 10% Pd/C (0.016 g, 10 mol %). The mixture was heated to reflux under $N_2$ for 18 h then cooled and filtered. The catalyst was rinsed with methanol and the filtrate was concentrated in vacuo to afford 0.113 g (98%) of the title alcohol as an off-white solid.

$^1$H NMR (CD$_3$OD) δ8.46 (m, 1H), 7.47 (m, 1H), 7.38–7.31 (m, 2H), 4.40 (m, 1H), 4.36 (m, 1H), 4.18 (m, 1H), 3.91 (m, 2H), 2.68 (s, 3H).

EXAMPLE 10

Protic Acid Catalyzed Preparation of [(2S)-8-Methyl-2,3-Dihydro[1,4]Dioxino[2,3-f]Quinolin-2-yl]Methanol

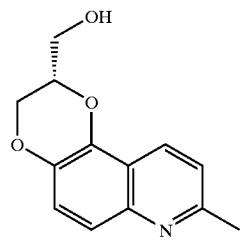

A mixture of crude (2S)-2[(benzyloxy)methyl-2,3-dihydro[1,4]dioxino [2,3-f]-quinoline product mixture (57.6 g, 0.179 mol) from example 7 in toluene (300 mL) was mixed with 20% HCl (436 g, 3.59 mol) and heated at 80° C. After 30 min, the reaction mixture was cooled to room temperature. The two layers were separated. A 30% $NH_4OH$ solution (400 mL) was added to the aqueous layer at 10–20° C. to pH 10. This was stirred for 30 min, the solid was filtered, washed with water and recrystallized from $CH_3OH$ (200 mL) to give 25.7 g (61.9%) of the title alcohol as an off-white solid.

EXAMPLE 11

Preparation of [(2R)-8-Methyl-2,3-Dihydro[1,4]Dioxino[2,3-f]Quinolin-2-yl]Methyl 4-Bromobenzenesulfonate

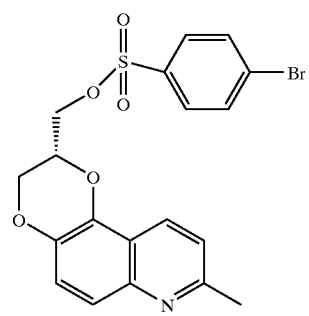

A solution of [(2S)-8-methyl-2,3-dihydro[1,4]dioxino[2,3-f]quinolin-2-yl]-methanol (4.0 g, 17.3 mmol), brosyl chloride (4.86 g, 19.0 mmol), dimethylamino pyridine (20 mg, 0.16 mmol) and triethylamine (3.62 mL, 25.8 mmol) in toluene (40 mL) was stirred at 60° C. for 6 h. The reaction mixture was cooled to room temperature then water (20 mL) was added. After 30 min, the two layers were separated. The organic layer was extracted with 8% $NaHCO_3$ (20 mL) and $H_2O$ (20 mL), dried over $Na_2SO_4$, filtered and concentrated in vacuo. The solid obtained was dissolved in isopropyl alcohol (50 mL) and toluene (10 mL) at 80° C., cooled to room temperature over 1 h then filtered, washed with (5:1) IPA: toluene (2×5 mL) and dried in a vacuum oven to give 5.99 g (76.9%) of the title compound as an off-white solid.

$^{13}$C NMR (CDCl$_3$) δ157.9, 144.3, 138.1, 134.7, 132.9, 129.7, 129.6, 129.0, 122.4, 121.7, 121.3, 118.8, 70.7, 67.6, 64.5, 25.4

EXAMPLE 12

Preparation of [(2R)-8-Methyl-2,3-Dihydro[1,4]
Dioxino[2,3-f]Quinolin-2-yl]Methyl 4-
Methylbenzenesulfonate

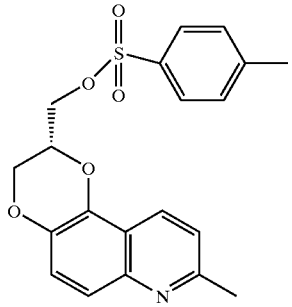

A solution of [(2S)-8-methyl-2,3-dihydro[1,4]dioxino[2,3-f]quinolin-2-yl]-methanol (0.13 g, 0.57 mmol), tosyl chloride (0.16 g, 0.82 mmol) and triethylamine (0.65 mL, 4.7 mmol) in $CH_2Cl_2$ (8 mL) was stirred at room temperature for 18 h. $CHCl_3$ (30 mL) and $H_2O$ (30 mL) were added. The two layers were separated. The aqueous layer was extracted with $CHCl_3$ (20 mL). The combined organic layers were dried over $Na_2SO_4$, filtered and concentrated in vacuo. Purification on $SiO_2$, eluting with (1:1) hexane:EtOAc gave 0.19 g (88%) of the title compound as a brown syrup.

$R_f$=0.43 ($CHCl_3$:iPrOH);

mp: 115–117° C.;

$^1$H NMR ($CDCl_3$) δ8.12 (d, J=8.6 Hz, 1H), 7.76 (m, 2H), 7.51 (d, J=9 Hz, 1H), 7.20–7.60 (m, 4H), 4.5–4.6 (m, 1H), 4.2–4.4 (m, 3H), 4.1–4.2 (m, 1H), 2.70 (s, 3H);

$^{13}$C NMR (DMSO) δ156.9, 145.4, 143.6, 137.9, 134.7, 132.2, 130.4, 128.7, 128.0, 121.8, 121.6, 121.3, 121.3, 118.3, 70.9, 68.6, 64.1, 60.1, 24.9, 21.4, 21.1, 14.4; GC/MS 385, 213, 186, 174, 145, 130, 117, 102, 91, 77, 65, 52, 41, 30;

IR (KBr): $υ_{max}$ 3625, 3374, 2924, 1732, 1628, 1601, 1573, 1485, 1359, 1251, 1177, 1096, 1049, 941, 818, 664, 554 $cm^{-1}$.

EXAMPLE 13

Formation of 3-(1,2,3,6-Tetrahydropyridin-4-yl)-1H-Indole

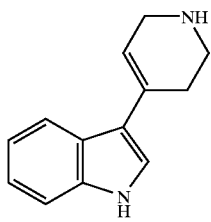

A mixture of indole (1.01 g, 8.59 mmol), 4-piperidone monohydrate hydrochloride (1.99 g, 12.9 mmol) and KOH (1.74 g, 31 mmol) in $CH_3OH$ (9 mL) was heated to reflux for 21 h. After cooling the reaction mixture to room temperature, $H_2O$ (14 mL) was added. The suspension was filtered, the solid was washed with (1:1) $MeOH:H_2O$ (20 mL) and air-dried to give 1.49 g (87%) of the title compound as an off-white solid.

$^1$H NMR (DMSO) δ11.1 (s, 1H), 7.80 (d, J=8.0 Hz, 1H), 7.3–7.5 (m, 2H), 7.0–7.2 (m, 2H), 6.16 (m, 2H), 3.3–3.5 (m, 2H), 2.9 (t, J=5.7 Hz, 2H), 2.38 (m, 2H);

$^{13}$C NMR (DMSO) δ137.0, 130.1, 124.7, 122.3, 121.1, 120.1, 119.9, 119.1, 116.7, 111.7, 45.0, 43.0, 40.1, 39.9, 39.7, 39.5, 39.3, 39.3, 39.1, 38.9, 28.3.

EXAMPLE 14

Preparation of (2S)-2-[4-(1H-Indol-3-yl)-3,6-
Dihydro-2H-Pyridin-1-ylmethyl]-8-Methyl-2,3-
Dihydro-1,4-Dioxino [2,3-f]Quinoline

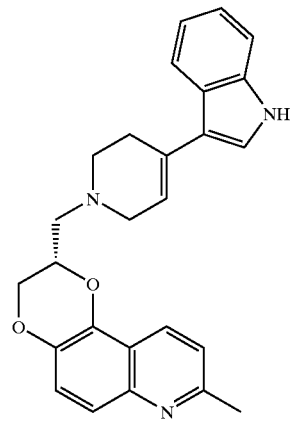

A solution of [(2R)-8-methyl-2,3-dihydro[1,4]dioxino[2,3-f]quinolin-2-yl]methyl 4-methylbenzenesulfonate (0.192 g, 0.499 mmol), 3-(1,2,3,6-tetrahydropyridin-4-yl)-1H-indole (0.119 g, 0.601 mmol) and $K_2CO_3$ (0.104 g, 0.753 mmol) in (1:1) THF:DMF (1.4 mL) was heated to 80–83° C. for 10 h. After this time, $H_2O$ (3 mL) was added and the suspension was filtered. The filtered solid was washed with $CH_3OH$ (2×3 mL), $Et_2O$ (2×5 mL) and air-dried to give 0.148 g (72%) of the title compound as a tan solid.

$R_f$=0.18 (EtOAc);

$^1$H NMR (DMSO) δ11.1 (s, 1H), 8.26 (d, J=8.6 Hz, 1H), 7.82 (d, J-7.8 Hz, 1H), 7.25–7.50 (m, 4H), 6.9–7.2 (m, 2H), 6.14 (s, 1H), 4.4–4.7 (m, 2H), 4.0–4.2 (m, 1H), 2.7–3.0 (m, 4H), 2.4–2.7 (m, 8H);

$^{13}$C NMR (DMSO) δ156.8, 146.8, 143.6, 138.4, 137.3, 135.6, 130.0, 128.9, 125.0, 123.1, 121.8, 121.6, 121.5, 121.2, 120.4, 119.6, 118.5, 117.9, 116.2, 112.1, 72.1, 66.8, 58.0, 53.8, 51.1, 28.9, 24.9;

IR (KBr): $υ_{max}$ 3410, 3240, 3059, 2848, 1601, 1484, 1403, 1352, 1255,1096, 982, 818, 745 $cm^{-1}$.

EXAMPLE 15

Preparation of (2S)-2-[4-(1H-Indol-3-yl)-3,6-Dihydro-2H-Pyridin-1-ylmethyl]-8-Methyl-2,3-Dihydro-1,4-Dioxino [2,3-f]Quinoline

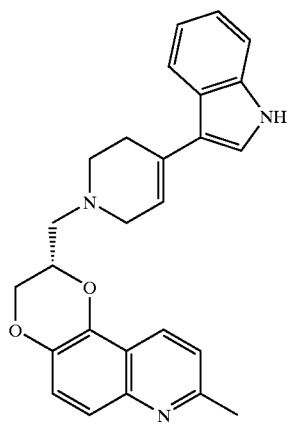

A solution of [(2R)-8-methyl-2,3-dihydro[1,4]dioxino[2,3-f]quinolin-2-yl]methyl 4-bromobenzenesulfonate (2.0 g, 4.44 mmol), 3-(1,2,3,6-tetrahydropyridin-4-yl)-1H-indole (1.01 g, 5.09 mmol) and diisopropylethyl amine (0.86 g, 6.65 mmol) in DMSO (10 mL) was heated to 80–83° C. After 10 h, the reaction mixture was cooled to 65–70° C. before CH$_3$OH (3 mL) was added. The resulted suspension was cooled to room temperature, filtered, washed with CH$_3$OH and dried in a vacuum oven to give 1.3 g (71%) of the title compound as a yellow solid.

EXAMPLE 16

Preparation of (2R)-1-(Benzyloxy)-3-[5-Bromo-2-Methyl-6-Quinolinyl)Oxyl]-2-Propanol from 5-Bromo-2-Methyl-6-Quinolinol

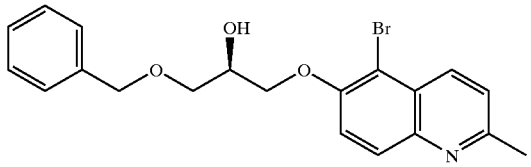

A solution of 5-bromo-2-methyl-6-quinolinol (2.50 g, 10.5 mmol), (S)-benzyl glycidyl ether (2.1 g, 12.8 mmol) and triethylamine (0.54 g, 5.3 mmol) in DMA (25 mL) was heated in a 80–83° C. oil bath for 2 d. The solution was cooled and poured into water (20 mL) while stirring. The tan precipitate formed was filtered, washed with water (10 mL) and dried in a vacuum oven to give 3.0 g (71%) of the title compound as a tan solid.

EXAMPLE 17

Preparation of 1-(Benzyloxy)-3-[5-Bromo-2-Methyl-6-Quinolinyl)Oxyl]-2-Propanol from 5-Bromo-2-Methyl-6-Quinolinol Salt

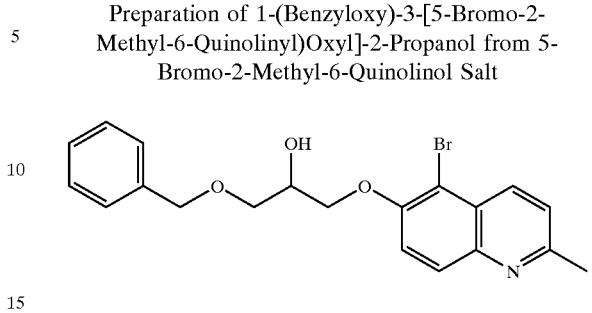

A solution of 5-bromo-2-methyl-6-quinolinol (1.0 g, 4.2 mmol), benzyl glycidyl ether (0.83 g, 5.1 mmol) and triethylamine (0.21 g, 2.1 mmol) in DMA (15 mL) was heated in a 90–95° C. oil bath for 18 h. The solution was cooled and poured into water (30 mL) and Et$_2$O (100 mL). The two layers were separated. The aqueous layer was extracted with Et$_2$O (2×50 mL). The organic layers were dried over Na$_2$SO$_4$, filtered and concentrated in vacuo to give 1.3 g (74%) of the titled compound as a tan solid.

EXAMPLE 18

Palladium Catalyzed Preparation of (2R)-2[(Benzyloxy)methyl]-8-methyl-2,3-Dihydro[1,4]Dioxino[2,3-f]Quinoline

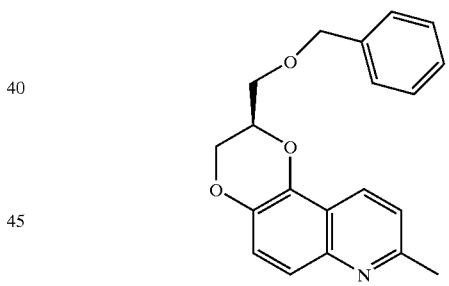

A mixture of (2R)-1-(benzyloxy)-3-[5-bromo-2-methyl-6-quinolinyl)oxyl]-2-propanol (2.9 g, 7.2 mmol) and NaH (0.48 g, 12 mmol) in toluene (15 mL) was stirred in a 50–52° C. oil bath for 40 min. This was then canulated into a mixture of Pd(OAc)$_2$ (82 mg, 0.36 mmol) and racemic BINAP (451 mg, 0.724 mmol) in toluene (10 mL) in a 50–52° C. oil bath. The resulted reaction mixture was degassed 3 times with Ar before heated to 100–102° C. in an oil bath. After 20 h, the reaction mixture was cooled to room temperature then sat'd NH$_4$Cl (60 mL) and EtOAc (60 mL) were added. This was stirred for 20 min before filtering through a bed of celite. The two layers were separated. The organic layer was dried over Na$_2$SO$_4$, filtered and concentrated in vacuo. Purification on SiO$_2$, eluting with (3:1) hexane:EtOAc gave 1.4 g (56%) of the title compound as a brown oil.

EXAMPLE 19

Palladium Catalyzed Preparation of 2[(Benzyloxy)methyl]-8-methyl-2,3-Dihydro[1,4]Dioxino[2,3-f]Quinoline

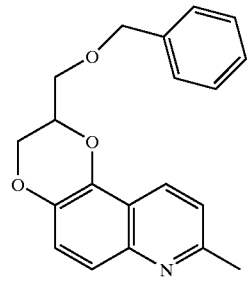

A mixture of 1-(benzyloxy)-3-[5-bromo-2-methyl-6-quinolinyl)oxyl]-2-propanol (1.1 g, 2.7 mmol) and NaH (175 mg, 4.4 mmol) in toluene (10 mL) was stirred in a 50–52° C. oil bath for 30 min. This was then canulated into a mixture of Pd(OAc)$_2$ (31 mg, 0.14 mmol) and (R)-Tol-BINAP (186 mg, 0.274 mmol) in toluene (10 mL) in a 50–52° C. oil bath. The resulted reaction mixture was degassed 3 times with Ar before heated to 100–102° C. in an oil bath. After 18 h, the reaction mixture was cooled to room temperature then sat'd NH$_4$Cl (30 mL) and EtOAc (30 mL) were added. This was filtered through a bed of celite. The two layers were separated. The aqueous layer was extracted with EtOAc (2×20 mL). The organic layers were combined, dried over Na$_2$SO$_4$, filtered and concentrated in vacuo. Purification on SiO$_2$, eluting with (3:1) hexane:EtOAc gave 0.52 g (58%) of the title compound as a yellow oil.

EXAMPLE 20

Preparation of [8-Methyl-2,3-Dihydro[1,4]Dioxino[2,3-f]Quinolin-2-yl]Methyl 4-Methylbenzenesulfonate

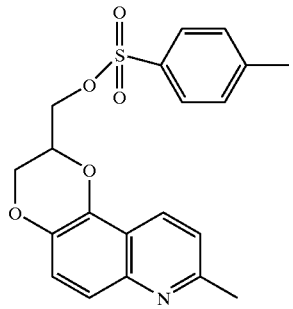

A solution of [8-methyl-2,3-dihydro[1,4]dioxino[2,3-f]quinolin-2-yl]-methanol (0.13 g, 0.57 mmol), tosyl chloride (0.16 g, 0.82 mmol) and triethylamine (0.65 mL, 4.7 mmol) in CH$_2$Cl$_2$ (8 mL) was stirred at room temperature for 18 h. CHCl$_3$ (30 mL) and H$_2$O (30 mL) were added. The two layers were separated. The aqueous layer was extracted with CHCl$_3$ (20 mL). The combined organic layers were dried over Na$_2$SO$_4$, filtered and concentrated in vacuo. Purification on SiO$_2$, eluting with (1:1) hexane:EtOAc gave 0.19 g (88%) of the title compound as a brown syrup.

R$_f$=0.44 (EtOAc);

$^1$H NMR (CDCl$_3$) δ8.12 (d, J=8.6 Hz, 1H), 7.76 (m, 2H), 7.51 (d, J=9 Hz, 1H), 7.20–7.60 (m, 4H), 4.5–4.6 (m, 1H), 4.2–4.4 (m, 3H), 4.1–4.2 (m, 1H), 2.70 (s, 3H), 2.39 (s, 3H).

EXAMPLE 21

Lewis Acid Catalyzed Preparation of [8-Methyl-2,3-Dihydro[1,4]Dioxino[2,3-f]Quinolin-2-yl]Methanol To a solution of 2[(benzyloxy)methyl-8-methyl-2,3-dihydro[1,4]dioxino [2,3-f]quinoline (0.30 g, 0.94 mmol) in CH$_2$Cl$_2$ (8 mL) being cooled in an ice-bath, FeCl$_3$ (0.77 g, 4.7 mmol) was added. After 1 h, the ice-bath was removed and the reaction mixture was stirred for another 4 h. CH$_2$Cl$_2$ (30 mL) and 1N NaOH (25 mL) were added to result in a suspension which was then filtered. The filtered solid was washed with CH$_3$OH (50 mL). The combined organic layers were concentrated in vacuo. Purification on SiO$_2$, eluted with (10:1) CHCl$_3$:iPrOH gave 0.15 g (68%) of the title compound as an off-white solid.

What is claimed is:

1. A method of making compounds of Formula I:

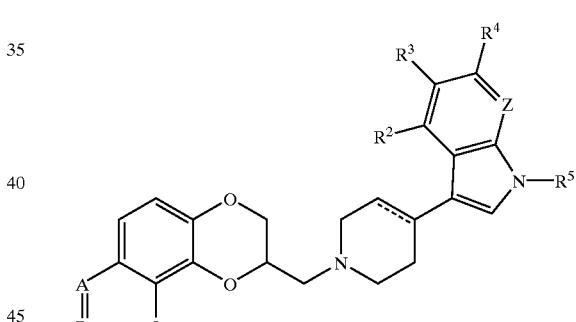

wherein

R$^1$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

R$^2$, R$^3$, R$^4$, and R$^6$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms R$^5$ is hydrogen or alkyl of 1 to 6 carbon atoms;

A dotted line represents an optional double bond;

A and D are selected from carbon, substituted by $R^1$, and nitrogen, provided that at least one of A and D is nitrogen;

E and G are carbon, substituted by $R^1$; and

Z is N or $CR^6$;

or pharmaceutically acceptable salts thereof, comprising the steps of:

a) halogenating a compound of the formula:

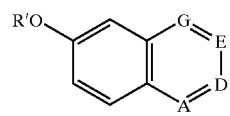

2 wherein $R^1$ is alkyl of 1–6 carbon atoms;

with a halogenating reagent to afford a compound of the formula:

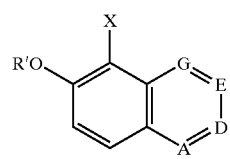

3 wherein X is Br, Cl, or I;

b) dealkylating the compound of Formula 3 in an acid to afford a compound of the formula:

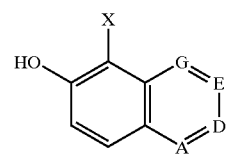

4 c) alkylating the compound of Formula 4 with R" protected glycidyl ethers

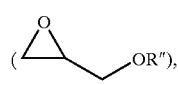

wherein R" is benzyl or substituted benzyl to afford compound of the formula:

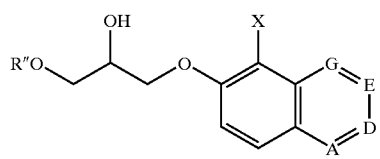

5 d) cyclizing the compound of Formula 5 with palladium or copper catalyst to afford a compound of the formula:

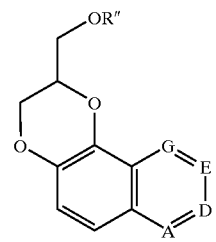

6 e) debenzylating the compound of Formula 6 to afford the compound of the formula:

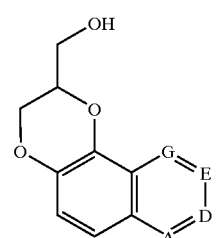

7 f) activating the hydroxy moiety of the compound of Formula 7 with a sulfonating reagent to afford a compound of the formula:

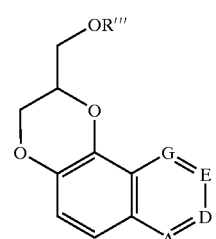

8 wherein R'" is an aryl- or alkyl- sulfonate; and g) coupling the compound of Formula 8 with the appropriate azaheterocycle of Formula 9

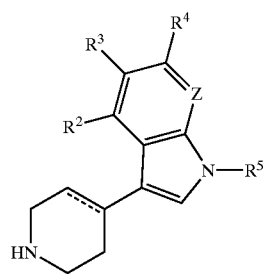

9 in the presence of base to provide a compound of Formula I

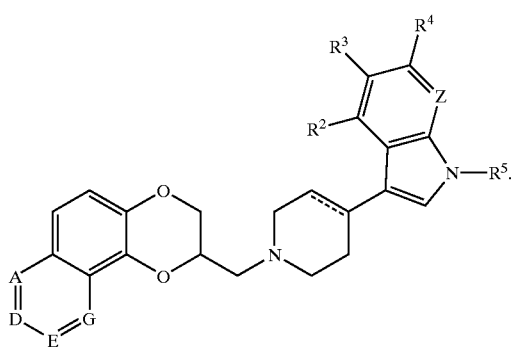

2. A method of making compounds of formula I:

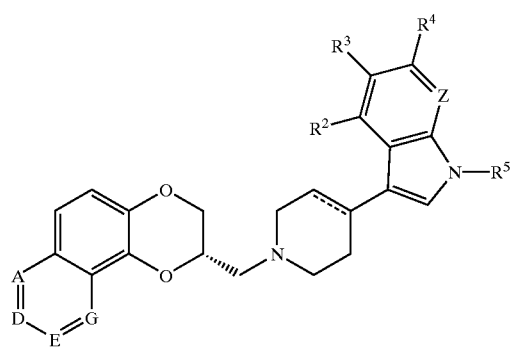

wherein

- $R^1$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
- $R^2$, $R^3$, $R^4$, and $R^6$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms
- $R^5$ is hydrogen or alkyl of 1 to 6 carbon atoms;
- A dotted line represents an optional double bond;
- A and D are selected from carbon substituted by $R^1$ and nitrogen, provided that at least one of A and D is nitrogen;
- E and G are carbon, substituted by $R^1$; and
- Z is N or $CR^6$;

or pharmaceutically acceptable salts thereof, comprising the steps of
a) halogenating a compound of the formula:

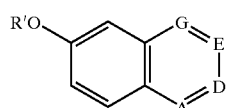

wherein R' is alkyl of 1–6 carbon atoms;

with N-halosuccinimide in a solvent to afford a compound of the formula:

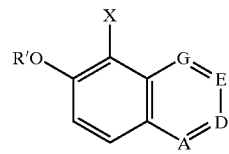

wherein X is Br, Cl, or I;

b) dealkylating the compound of Formula 3 in an acid to afford a compound of the formula:

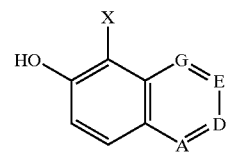

c) alkylating the compound of Formula 4 with R″ protected glycidyl ethers

wherein R″ is benzyl or substituted benzyl, or alkyl alcohol of 1 to 6 carbon atoms to afford compound of the formula:

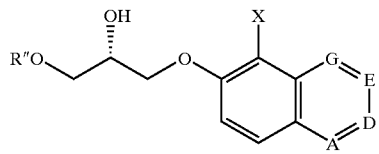

d) cyclizing the compound of Formula 5 with palladium or copper catalyst to afford a compound of the formula:

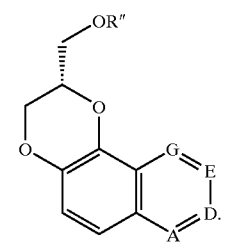

e) debenzylating the compound of Formula 6 to afford the compound of the formula:

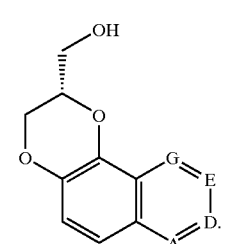

f) activating the hydroxy moiety of the compound of Formula 7 with alkyl- or aryl- sulfonyl chloride or with alkyl or aryl sulfonic anhydride in the presence of a base to afford a compound of the formula:

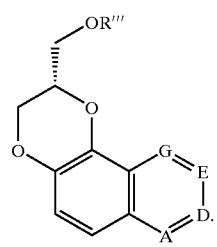
8 wherein R''' is an alkyl- or aryl-sulfonate; and g) coupling the compound of Formula 8 with the appropriate azaheterocycle of Formula 9

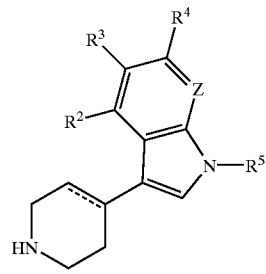
9 in the presence of base to provide a compound of Formula I.

3. A method of making compounds of formula Ia:

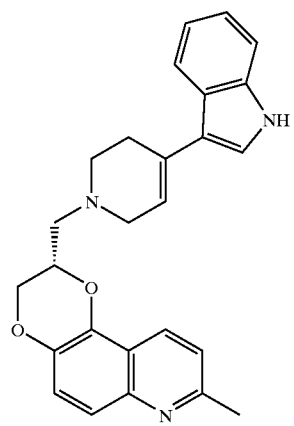
Ia comprising the steps:

a) halogenating a compound of the formula:

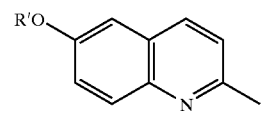
2 wherein R' is alkyl of 1–6 carbon atoms;
with N-halosuccinimide in a solvent to afford a compound of the formula:

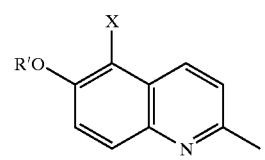
3 wherein X is Br, Cl, or I;

b) dealkylating the compound of Formula 3 in an acid to afford a compound of the formula:

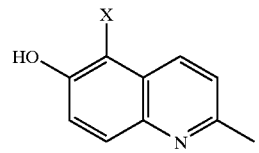
4 c) alkylating the compound of Formula 4 with R'' protect glycidyl ethers

wherein R'' is benzyl or substituted benzyl;
to afford compound of the formula:

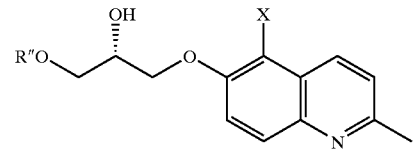
5 d) cyclizing the compound of Formula 5 with palladium or copper catalyst to afford a compound of the formula:

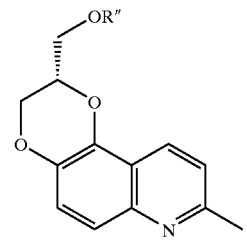
6 e) debenzylating the compound of Formula 6 to afford the compound of the formula:

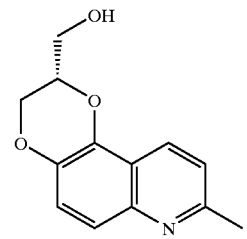
7 f) activating the hydroxy moiety of the compound of Formula 7 with alkyl or aryl sulfonyl chloride with alkyl or aryl sulfonic anhydride in the presence of a base to afford a compound of the formula:

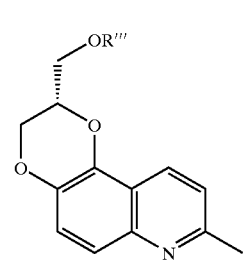
8 wherein R''' is a alkyl- or aryl-sulfonate; and g) coupling the compound of Formula 8 with 3-tetrahydropyridinyl-indole in the presence of base to provide a compound of Formula Ia.

4. The method of claim 1 wherein the compound of Formula 2 is treated with N-halosuccinimide in acetonitrile.

5. The method of claim 1 wherein the halogenation reaction is quenched with a 10% NaHSO3 solution and the product precipitated with NaOH.

6. The method of claim 1 wherein the compound of Formula 3 is dealkylated with a Lewis acid.

7. The method of claim 1 wherein the compound of Formula 3 is dealkylated with a protic acid.

8. The method of claim 7 wherein the protic acid is HBr.

9. The method of claim 8 wherein the compound of Formula 2 is heated to reflux in HBr for from about 6 to about 7 hours.

10. The method of claim 1 wherein the compound of Formula 4 is alkylated with benzyl- or substituted benzyl-glycidyl ether in a polar solvent.

11. The method of claim 1 wherein the compound of Formula 4 is alkylated with benzyl glycidyl ether, 4-bromobenzyl glycidyl ether, 4-chlorobenzyl glycidyl ether, 3,4-dimethoxybenzyl glycidyl ether, 2- or 4-nitrobenzyl glycidyl ether, or 4-methoxy-phenyl glycidyl ether.

12. The method of claim 10 wherein the polar solvent is dimethylsulfoxide, dimethyl-formamide, or dimethylacetamide.

13. The method of claim 10 wherein the base is triethylamine, sodium carbonate, or potassium carbonate.

14. The method of claim 1 wherein the compound of Formula 5 is cyclized using palladium catalyst in the presence of phosphine ligand and base.

15. The method of claim 14 wherein the palladium catalyst is tris(dibenzylidene-acetone)dipalladium, tetrakis(triphenylphosphine)palladium, or palladium acetate with phosphine ligands selected from the group consisting of (±) 2,2'-bis(diphenylphosphino)-1,1'-binaphthyl and separate enantiomers thereof; (±) 2,2'-bis(di-p-tolyl-phosphino)-1,1'-binaphthyl and separate enantiomers thereof; 1-1'-bis(diphenylphosphino)ferrocene; 1,3-bis(diphenyl-phosphino)propane; and 1,2-bis(diphenylphosphino)ethane.

16. The method of claim 14 wherein the base is sodium hydride, lithium hydride, potassium hydride, potassium carbonate, sodium carbonate, titanium carbonate, cesium carbonate, potassium t-butoxide or potassium phosphate tribasic.

17. The method of claim 1 wherein the compound of Formula 5 is cyclized using copper catalyst in the presence of base.

18. The method of claim 17 wherein the copper catalyst is copper iodide.

19. The method of claim 17 wherein the base is sodium hydride, lithium hydride or potassium hydride.

20. The method of claim 1 wherein the compound of Formula 6 is debenzylated with Lewis acid, strong protic acid or under reductive cleavage conditions.

21. The method of claim 20 wherein the Lewis acid is boron tribromide, boron trichloride, aluminum trichloride, ferric chloride or trimethylsilyl iodine.

22. The method of claim 20 wherein the protic acid is hydrobromic acid or hydrochloric acid.

23. The method of claim 1 wherein a) the compound of Formula 5 is cyclized using copper catalyst in the presence of NaI to provide compound of Formula 6, and b) compound of Formula 6 is debenzylated with HCl to provide compound of Formula 7.

24. The method of claim 20 wherein reductive cleavage is performed using palladium catalyst and hydrogen transfer reagents.

25. The method of claim 24 wherein the palladium catalyst is Pd/C.

26. The method of claim 24 wherein the transfer reagent is cyclohexene, methylcyclohexene, ammonium formate or hydrogen.

27. The method of claim 24 wherein the palladium catalyst is Pd/C and the transfer reagent is cyclohexene.

28. The method of claim 1 wherein the compound of Formula 7 is activated with a sulfonating reagent or with an aryl or alkyl sulfonic anhydride in the presence of a base.

29. The method of claim 28 wherein the compound of Formula 7 is activated with p-toluenesulfonyl chloride, methanesulfonyl chloride, 2-, 3- or 4-nitrobenzenesulfonyl chloride, 2- or 4-bromobenzenesulfonyl chloride or trifluoromethylsulfonic anhydride.

30. The method of claim 28 wherein the compound of Formula 7 is activated with 4-bromobenzenesulfonylchloride.

31. The method of claim 28 wherein the base is triethylamine or pyridine in methylene chloride, tetrahydrofuran, or toluene.

32. The method of claim 1 wherein the compound of Formula 8 is coupled with an azaheterocycle of Formula 9 in the presence of a base.

33. The method of claim 32 wherein the base is sodium carbonate, potassium carbonate, or Hünig's base.

34. A method of making compounds of Formula I:

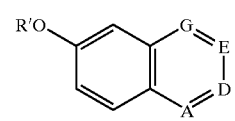

wherein $R^1$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2, R^3, R^4$, and $R^6$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms $R^5$ is hydrogen or alkyl of 1 to 6 carbon atoms;

A dotted line represents an optional double bond;

A and D are selected from carbon, substituted by $R^1$, and nitrogen, provided that at least one of A and D is nitrogen;

E and G are carbon, substituted by $R^1$; and

Z is N or $CR^6$;

or pharmaceutically acceptable salts thereof, comprising the steps of:

a) halogenating a compound of the formula:

wherein R' is alkyl of 1–6 carbon atoms;

with N-halosuccinimide in a solvent to afford a compound of the formula:

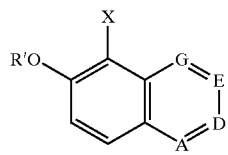
3 wherein X is Br, Cl, or I;

b) dealkylating the compound of Formula 3 in an acid to afford a compound of the formula:

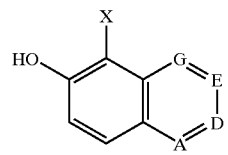
4 c) alkylating the compound of Formula 4 with R″ protected glycidyl ethers

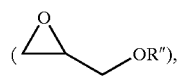

wherein R″ is benzyl or substituted benzyl to afford compound of the formula:

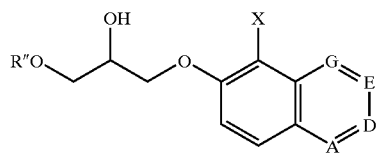
5 d) cyclizing the compound of Formula 5 with palladium or copper catalyst to afford a compound of the formula:

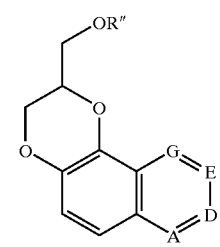
6 e) debenzylating the compound of Formula 6 to afford the compound of the formula:

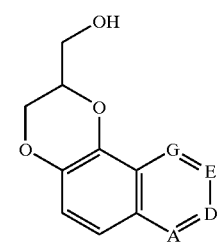
7 f) activating the hydroxy moiety of the compound of Formula 7 to a halide to afford a compound of the formula:

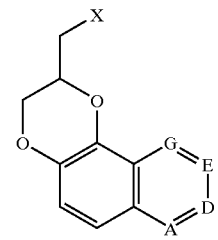
10 wherein X is I, Br or Cl and g) coupling the compound of Formula 10 with the appropriate azaheterocycle of Formula 9

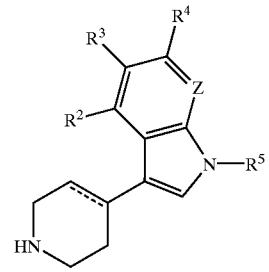
9 in the presence of base to provide a compound of Formula I.

35. The method of claim 34 wherein the compound of Formula 7 is activated with a halogenating reagent.

36. The method of claim 34 wherein the compound of Formula 7 is activated as a halide with phosphorous triiodide, phosphorous tribromide, phosphorous pentachioride or thionyl chloride.

37. A method of making compounds of Formula I:

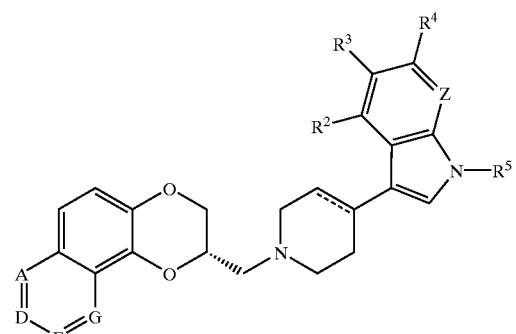
1 wherein $R^1$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2, R^3, R^4$, and $R^6$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms $R^5$ is hydrogen or alkyl of 1 to 6 carbon atoms;

A dotted line represents an optional double bond;

A and D are selected from carbon, substituted by $R^1$, and nitrogen, provided that at least one of A and D is nitrogen;

E and G are carbon, substituted by $R^1$; and

Z is N or $CR^6$;

or pharmaceutically acceptable salts thereof comprising the steps of:

a) halogenating a compound of the formula:

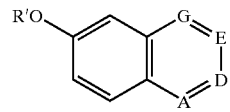

2 wherein R' is alkyl of 1–6 carbon atoms;
with N-halosuccinimide in a solvent to afford a compound of the formula:

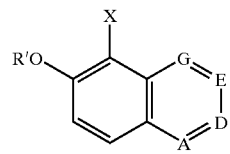

3 wherein X is Br, Cl, or I;

b) dealkylating the compound of Formula 3 in an acid to afford a compound of the formula:

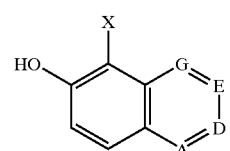

4 c) alkylating the compound of Formula 4 with R" protected glycidyl ethers

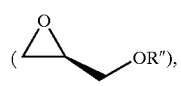

wherein R" is benzyl or substituted benzyl to afford compound of the formula:

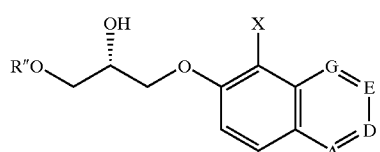

5 d) cyclizing the compound of Formula 5 with palladium or copper catalyst to afford a compound of the formula:

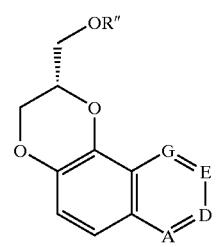

6 e) debenzylating the compound of Formula 6 to afford the compound of the formula:

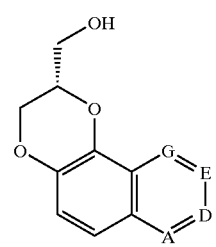

7 f) activating the hydroxy moiety of the compound of Formula 7 to a halide to afford a compound of the formula:

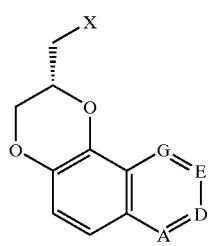

10 wherein X is I, Br or Cl; and g) coupling the compound of Formula 10 with the appropriate azaheterocycle of Formula 9

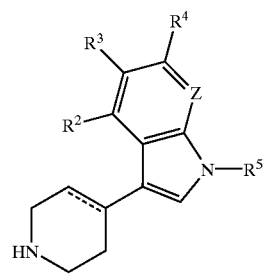

9 in the presence of base to provide a compound of Formula I.

38. A method of making a compound of Formula Ia:

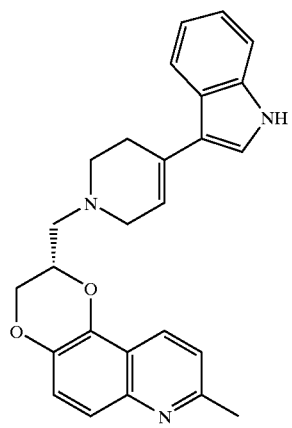

1a comprising the steps:

a) halogenating a compound of the formula:

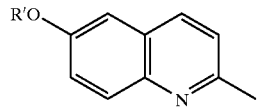

2a wherein R' is alkyl of 1–6 carbon atoms;

with N-halosuccinimide in a solvent to afford a compound of the formula:

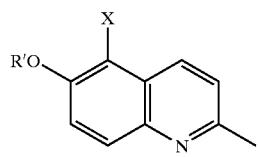

3a wherein X is Br, Cl, or I;

b) dealkylating the compound of Formula 3a in an acid to afford a compound of the formula:

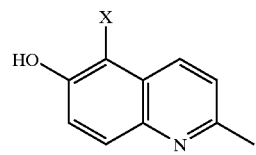

4a c) alkylating the compound of Formula 4a with R″ protected glycidyl ethers

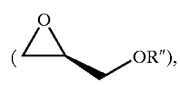

wherein R″ is benzyl or substituted benzyl; to afford compound of the formula:

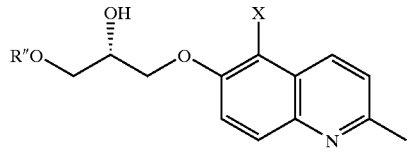

5a d) cyclizing the compound of Formula 5a with palladium or copper catalyst to afford a compound of the formula:

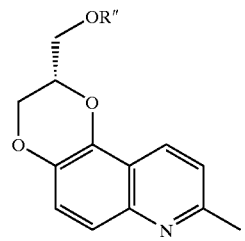

6a e) debenzylating the compound of Formula 6a to afford the compound of the formula:

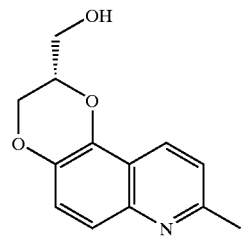

7a f) activating the hydroxy moiety of the compound of Formula 7a to a halide to afford a compound of the formula:

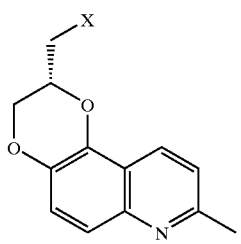

10a wherein X is I, Br or Cl; and g) coupling the compound of Formula 10a with 3-tetrahydropyridinyl-indole in the presence of base to provide a compound of Formula Ia.

* * * * *